United States Patent [19]

Smith

[11] Patent Number: 4,797,906

[45] Date of Patent: Jan. 10, 1989

[54] NONDESTRUCTIVE METHOD FOR ANALYZING TOTAL POROSITY OF THIN SECTIONS

[75] Inventor: Michael P. Smith, Tulsa, Okla.

[73] Assignee: Amoco Corporation, Chicago, Ill.

[21] Appl. No.: 101,880

[22] Filed: Sep. 28, 1987

[51] Int. Cl.$^4$ .......................................... G01N 23/223
[52] U.S. Cl. .......................................... 378/44; 378/48; 378/50; 250/255; 250/269
[58] Field of Search .................. 378/44, 47, 48, 50, 378/45; 250/252.1, 255, 269

[56] References Cited

U.S. PATENT DOCUMENTS 3,562,525  2/1971  Constantine .................... 378/48
4,510,573  4/1985  Boyce et al. .................... 250/269

Primary Examiner—Carolyn E. Fields
Assistant Examiner—David P. Porta

[57] ABSTRACT

Total porosity of impregnated thin sections can be measured using X-ray fluorescence. The technique requires an impregnating fluid which contains an element not contained in more than trace quantities by the rock. By measuring the intensity of fluorescence generated by bombarding the impregnated thin section with sufficiently energetic X-rays and rationing that intensity to the intensity of fluorescence generated by subjecting a sample containing only epoxy to the same conditions, and scaling the resulting measures of fluorescence, a measure of total effective porosity is produced.

6 Claims, 2 Drawing Sheets

NONDESTRUCTIVE METHOD FOR ANALYZING TOTAL POROSITY OF THIN SECTIONS

FIELD OF THE INVENTION

The invention relates to the analysis of porosity, particularly to the analysis of porosity of rock samples. In a particular aspect, the invention relates to analyzing total porosity of such rock samples.

SETTING OF THE INVENTION

Porosity is one of the two essential attributes of reservoir quality, the other being permeability. The pore spaces, or voids within a rock are generally filled with water, but contain oil or gas within a field. Porosity is either expressed as the void ratio which is the ratio of voids to solid rock, or more frequently, as a percentage. Pores can be of three morphological types: catenary, cul-de-sac, and closed. Catenary pores are those that communicate with others by more than one throat passage. Cul-de-sac or dead-end pores have only one throat passage connecting with another pore. Closed pores have no communication with other pores. Catenary and cul-de-sac pores constitute effective porosity in that hydrocarbons can emerge from them. In catenary pores, hydrocarbons can be flushed out by a natural or artificial water drive. Cul-de-sac pores are unaffected by flushing, but may yield some oil or gas by expansion as reservoir pressure drops. Closed pores are unable to yield hydrocarbons, or water. The ratio of total to effective porosity is extremely important, being directly related to the permeability of a rock.

Further, determining what portion of total effective porosity is due to macroporosity and what portion is due to microporosity is extremely significant in making the decision whether to produce a reservoir. Microporosity is a portion of total effective porosity that is invisible with an optical microscope but visible using a scanning electron microscope, containing pores small enough to hold water against the flow of gravity and to retard water flow. Macroporosity is that portion of total effective porosity containing pores of large enough size that water is not held in it by capillary action.

In the past, certain strata have not been produced because measurements of oil and water content indicated too high a water content. For example, measurements of oil and water content using data from resistivity tools have at times indicated a higher water content than met production criteria. A measurement of microporosity could have shown that a significant portion of the water was water bound in micropores, which would not have been produced. Had the water and oil content of the macropores been considered alone, decisions could have been made to produce the strata. Awareness of this has led to techniques for measuring total effective porosity being used with techniques for measurements of macroporosity, thereby permitting microporosity to be calculated. This, when used with techniques for measuring oil and water content, has led to economic production of reservoirs which in the past would not have been produced.

Total effective porosity can be measured in a number of ways directly from cores including the Washburn-Bunting Method (gas expansion technique), and the Boyle's Law Method. In the Washburn-Bunting technique, air within pores is extracted and the volume measured and compared with bulk volume determined, for example, by volume of mercury displaced by the sample. In the Boyle's Law Method, either an increase in volume of contained gas can be measured as pressure is decreased by a known amount, or grain size and bulk volume can be measured and porosity determined by difference.

Macroporosity can be measured by techniques such as impregnating a thin section with an epoxy resin having a dye therein and then visually estimating ("point counting"), or digitizing and determining relative area occupied by the dye compared to total area (image analysis), to give a measure of macroporosity. More direct measurements can be made on larger samples, for example, by saturating a core sample with water and then measuring water volume produced at predetermined pressure. These techniques for determining macroporosity are well known to those skilled in the art and need not be further described here.

However, the need exists for techniques capable of measuring total effective porosity on thin sections, and for more efficient and direct techniques for measuring total effective porosity generally.

SUMMARY OF THE INVENTION

In accordance with the invention, there is provided a method for determining total effective porosity of a rock sample. The rock sample is impregnated with a fluid under conditions effective for introducing the fluid into both macropores and micropores. The fluid contains elements capable of X-ray fluorescence when stimulated by X-rays. The impregnated rock sample is then stimulated with X-rays and the resulting X-ray fluorescence is detected and measured. A sample comprising only the fluid containing elements capable of X-ray fluorescence is also stimulated, and the resulting X-ray fluorescence is detected and measured. Then, by scaling or ratioing or dividing the X-ray fluorescence resulting from the stimulated impregnated rock sample with reference to or by the X-ray fluorescence resulting from the sample comprising the fluid only, a measure of total effective porosity is generated. According to a further aspect of the invention, background fluorescence resulting from a sample holder having neither rock nor fluid sample is used for correction of fluorescence data before deriving the measure of total effective porosity.

DETAILED DESCRIPTION OF THE INVENTION

Figure 1:
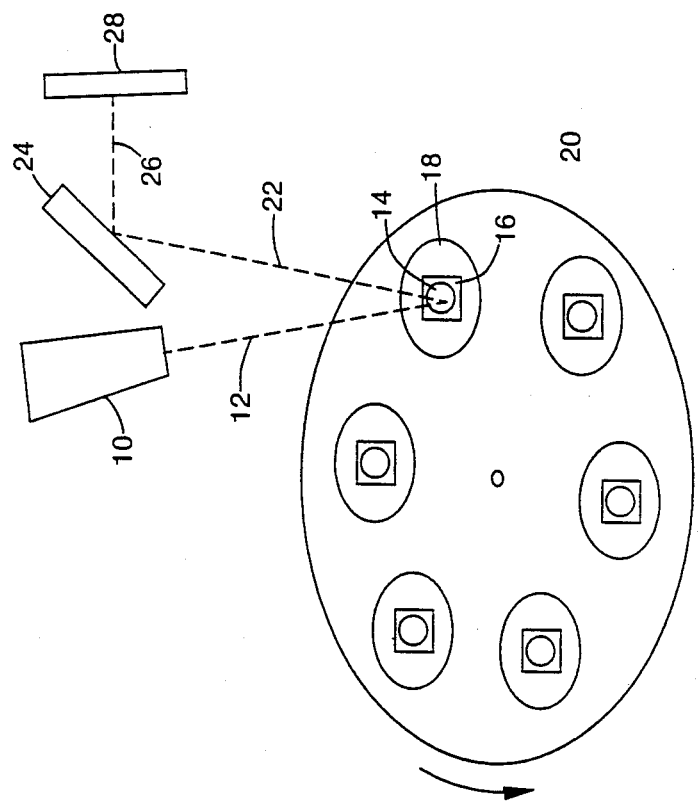
FIG. 1 illustrates the method of the invention in connection with a preferred apparatus.

According to a feature of the invention, a rock sample impregnated with a fluid containing elements capable of X-ray fluorescence is stimulated by X-rays and the resulting X-ray fluorescence is detected and measured.

The rock sample is impregnated with the fluid under conditions effective for introducing the fluid into both macropores and micropores of the rock sample. The epoxy impregnation can be carried out in the usual way for preparation of epoxy impregnated rock thin sections. Such preparation has been found to give measures of total effective porosity comparable to measures derived from the Boyle's Law Method. Such epoxy impregnation techniques are well known to those skilled in the art and need not be further described here. See also the Example below.

Elements fluoresce X-radiation that is characteristic of the atom of interest when bombarded with sufficient energy to eject an electron from one of the atom's inner shells. An outer shell electron then fills the inner shell vacancy thus created and the atom emits a photon, the energy of which equals the difference in energies between the two electron shells.

In X-ray fluorescence, the sample of interest is bombarded with high energy X-rays. If the X-rays are energetic enough, they will cause the atoms of interest to fluoresce, and they will cause those atoms to emit their characteristic X-radiation. To a very good first approximation, the fraction of the element of interest that the sample contains equals the ratio of the intensity of X-rays produced in the sample to the intensity of X-rays produced when irradiating the pure element under identical conditions. If a compound standard is used rather than a pure element standard, the amount of the element of interest in an unknown is given by:

$$C_u^a = \frac{K_u^a}{K_s^a} C_s^a$$

where:
$C_u^a$ = concentration of element $a$ in unknown (i.e., in the sample)

$C_s^a$ = concentration of element $a$ in standard $K_u^a$ = intensity of "$a$" X-rays in unknown $K_a^s$ = intensity of "$a$" X-rays in standard.

In most epoxy impregnated sedimentary rocks, the only substance that contains appreciable Cl is the epoxy. It is resonable to assume the epoxy to have a constant composition where the sample and the standard are prepared using the same batch of epoxy. Then, the amount of epoxy in an impregnated thin section equals:

$$(\% \text{ Epoxy})_{Thin\ Section} (C_{Epoxy}^{Cl}) = \frac{K_{Thin\ Section}^{Cl}}{K_{100\%\ Epoxy}^{Cl}} C_{Epoxy}^{Cl}$$

or $$(\% \text{ Epoxy})_{Thin\ Section} = \frac{K_{Thin\ Section}^{Cl}}{K_{100\%\ Epoxy}^{Cl}}$$

and since the % of Epoxy in the thin section equals the total effective porosity of the rock slice, we have $$\phi = \frac{K_{Thin\ Section}^{Cl}}{K_{Epoxy}^{Cl}}$$

when identical areas of thin section and epoxy are irradiated under identical conditions.

The rock sample can be any sample capable of having its surface placed in an X-ray beam for stimulation and detection of X-ray fluorescence. Preferably, the sample is a thin section prepared in the usual way by epoxy impregnation and sectioning of rock specimens.

The fluid can be any fluid which can be introduced into the pore spaces which constitutes the effective porosity of a sample. Preferably, the fluid is of a nature that is stable over time. For example, the fluid can preferably be an impregnation epoxy such as is conventionally used for thin section preparation and/or such as is conventionally used with a suitable dye for preparation of rock thin sections for macroporosity determinations by point counting or image analysis. Preferably, the fluid contains such a dye because, thus, total effective porosity determined in accordance with the invention and macroprosity can be determined for the same sample.

The element capable of X-ray fluorescence can be an element not contained in more than trace amounts by the rock being analyzed. Many commercially available impregnation epoxies have significant amounts of chlorine and chlorine usually occurs in only trace amounts in most sedimentary rocks. Therefore, for most rocks, off-the-shelf commercial impregnation epoxies can be used. For rocks having a significant chlorine content, for example, those containing a halite cement, the epoxy can be doped with a more exotic element, for example, iodine, bromine, and the like.

During X-ray fluorescence spectroscopy, the energy of exciting X-rays is kept as low as possible, but still energetic enough to fluoresce the X-ray line of interest. This is done to reduce or eliminate errors caused by secondary fluorescence of that line by a higher energy line from another element in the sample. This helps in avoiding secondary X-ray fluorescence, for example, from iron. Chlorine, bromine, and iodine meet these requirements. Other suitable elements include silver, cadmium, scandium, antimony, rubidium, or any other element not normally present in more than trace quantities in sedimentary rocks.

The X-ray stimulation of the impregnated rock sample and the detection and measurement of X-ray fluorescence is by X-ray fluorescence analysis. A specimen is irradiated by an X-ray beam and the lines in the spectrum of the resulting X-ray fluorescence are diffracted at various angles by a crystal with known lattice spacing. The intensity of the spectral lines characteristic of the fluorescing elements can be measured as an indication of the concentration of the element in the field being analyzed. The concentration of the element in the field being analyzed is in turn directly related to the amount of epoxy, and therefore, to the total effective porosity. Alternatively, energy dispersive X-ray fluorescence spectroscopy can be used.

The field on a rock or fluid sample subjected to X-ray irradiation can be defined by uniform masks made of a nonfluorescing material (at the wavelengths of interest) such as copper so that the same area is exposed on different samples.

X-ray take-off angle from the sample is preferably a high angle to minimize absorption of X-ray fluorescent emissions by by other portions of the rock sample. A take-off angle of 90° has been found to provide particularly good results. At this angle, absorption corrections become unnecessary.

According to a feature of the invention, a sample of the fluid containing elements capable of X-ray fluorescence is stimulated by X-rays and resulting X-ray fluorescence detected and measured. If samples are being prepared, the same epoxy used for impregnation of the rock specimens can be used to prepare the sample consisting of the fluid alone. If samples are being analyzed which have been prepared in the past, it is frequently possible to locate and mask an area on a section which consists only of the fluid. In both cases, preferably the same fluid is used for impregnated rock sample and reference fluid sample.

According to a further feature of the invention, background fluorescence can be measured using a sample holder and mask where neither rock sample nor fluid are present. The resulting fluorescence is a measure of the contribution of the sample holder and mask to the total fluorescence of rock sample and fluid and can be used to correct those data.

The detection can be, for example, by means of a flowthrough proportional detector which provides a count when a sufficiently energetic photon is emitted from a sample. The counts on different samples can be made for predetermined periods of time. As indicated sample holders without fluid or sample are preferably used to determine a level of background X-ray fluorescence which can be subtracted from X-ray fluorescence measurements of both fluid impregnated rock sample and fluid only sample.

Referring now to FIG. 1, X-ray source 10 produces a beam 12 which irradiates sample 14 partly covered by mask 16 in sample holder 18. X-ray fluorescence beam 22 is reflected from reflector 24, for example, a diffracting monochromator, and the reflected diffracted beam 26 of a predetermined characteristic wavelength is provided to detector 28 where a count is registered for a preselected period of time. The take-off angle of beam 26 is preferably as close to perpendicular to the surface of the sample as possible. Rotation of the sample carrier 20 in the direction shown by the arrow positions other sample holders in position for X-ray irradiation.

Measures of X-ray fluorescence from rock samples and from fluid samples preferably after correction for background fluorescence due to sample, slide, holder, and the like, can be scaled relative to one another (for example, by ratioing or scaling or division) to give a measure of total effective porosity. Preferably, this step is performed after correcting the data for background fluorescence due to the sample holder and mask without rock sample and impregnating fluid.

According to a further aspect of the invention, a feature of the invention is measuring macroporosity and then determining microporosity as the difference between the measurement of total effective porosity and the measure of macroporosity.

EXAMPLE

1. Boyle's Law Porosity

The total effective porosities of a series of rock samples of known volumes are measured using the Boyle's Law Method. The samples are loaded into a vacuum chamber and evacuated. Gas is then allowed to enter the chamber until a certain pressure is obtained. The amount of gas required to reach this pressure is noted, and total porosity is then calculated using the gas law:

$PV = nRT$ where
  P = pressure
  V = volume
  R = gas constant
  n = moles of gas
  T = absolute temperature
This can be rearranged as $V_{Total} = nRT/P$ Since R, T, and P are held constant $V_{Total} = nK$ when $K = $ a constant $= RT/R$ and since $V_{Total} = V_{Chamber} + \theta_{Rock}$ then $\theta_{Rock} = nK - V_{Chamber}$ The results are shown in Table 1.

TABLE 1

| Specimen | Effective Porosity (%) |
| --- | --- |
| 1 | 11.8 |
| 2 | 24.1 |
| 3 | 15.4 |
| 4 | 13.5 |
| 5 | 10.4 |
| 6 | 21.3 |
| Standard | 100.0 |

2. X-ray Fluorescence Measures of Porosity

A. Sample Preparation

A block of rock about ¼ inch thick, for each of the series of rock samples, is placed in a series of receptacles. Liquid epoxy (prepared by mixing 190 grams Dow Epoxy Resin 331, 55 milliliters n-butyl-glycidyl ether, 24 milliliters diethylene-triamine and 1.5 grams Kriegrosol Blue Supra concentrated powder—a blue dye suitable for point counting determination of macroporosity) is poured over each sample of the rock so that it is completely covered. The epoxy covered rocks are loaded into a high-vacuum, high-pressure cell. High vacuum of about 100 Torr is pulled in the chamber for about 30 minutes, causing the rocks to degas and epoxy to begin to infill the pore system. This is followed by the application of 1200 psi nitrogen ($N_2$) gas. The samples are left under high pressure overnight. The application of high pressure drives the epoxy deep into the pores, so that all or nearly all the pores are filled with epoxy. The epoxy cures overnight, and is hardened when the sample is removed from the pressure vessel. Thin sections about 30 microns in thickness of the epoxy impregnated rocks are mounted on sample slides and masked having an exposed circular sample area about ¾ in. in diameter.

B. X-ray Fluorescence

The series of rock section sections are placed on a sample tray and X-ray fluorescence is measured using an S.Max-E/5 X-ray Fluorescence Spectrometer (available from Rigaku Industrial Corporation, Osaka, Japan). For each sample and for the epoxy standard, counts of $K\alpha$ photons are made for 400 seconds. The incident X-radiation is generated by passing 50 milliamps of current through a rhodium tube and accelerating the electrons by a 22.5 kilivolt potential. The results are shown in Table 2.

TABLE 2

| Specimen | Chlorine $K\alpha$ (Counts/400 sec) |
| --- | --- |
| 1 | 20,777 |
| 2 | 47,753 |
| 3 | 25,910 |
| 4 | 25,215 |
| 5 | 20,677 |
| 6 | 37,621 |
| Standard | 159,760 |

Background fluorescence measured using a mask sample slide having neither sample nor impregnating epoxy was about 5000 counts/400 seconds.

Figure 2:
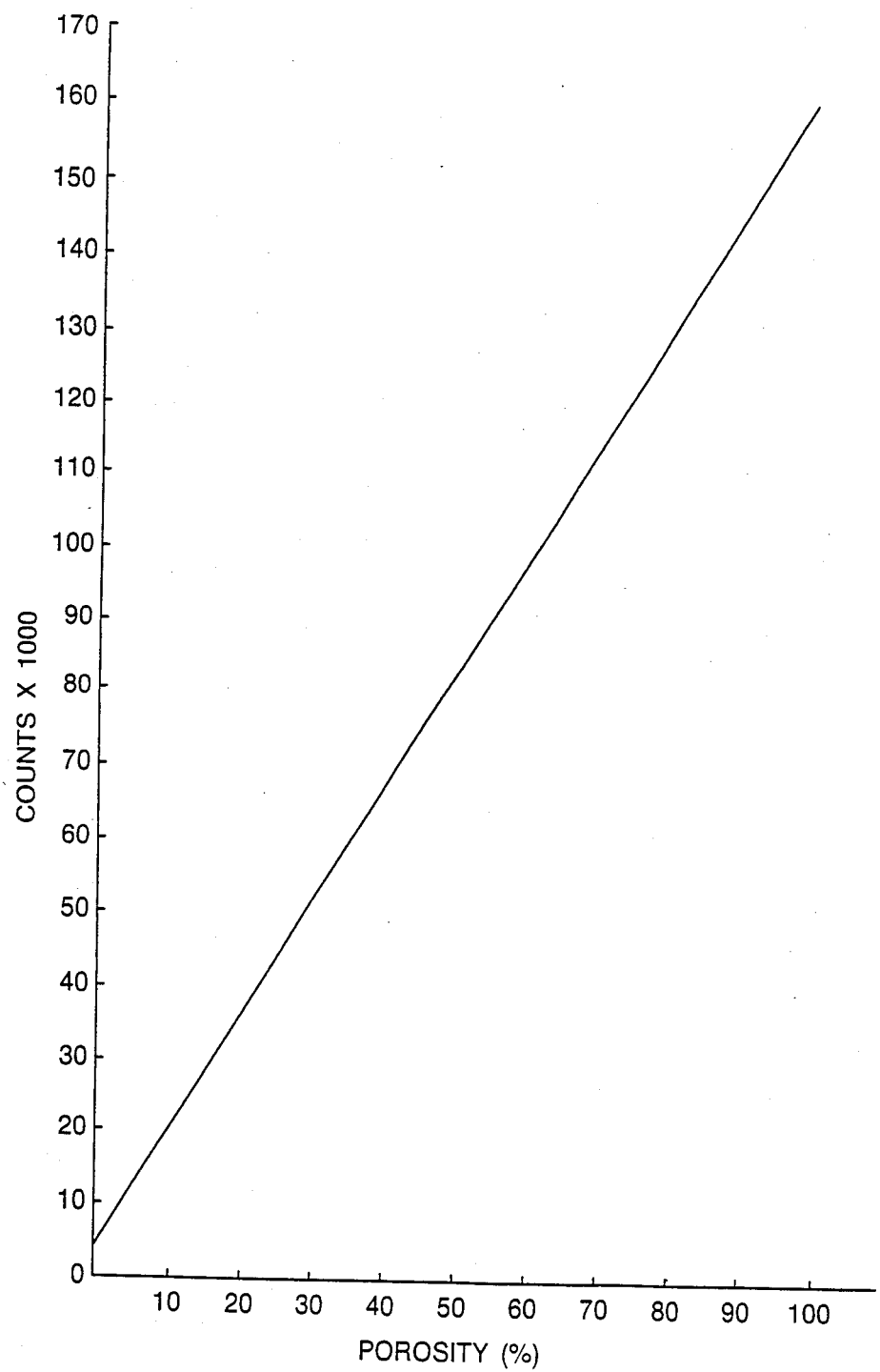
FIG. 2 shows correlation between total effective porosity determined by Boyle's Law Method and Fluorescence Data in accordance with the invention.

The results of Table 1 and Table 2 are plotted in FIG. 2. As therein shown, the two sets of data are linearly related indicating that X-ray fluorescence of selected elements can be used to generated measures of total effective porosity.

Porosities from Table 1 and porosities determined from the data of Table 2 after correction for background fluorescence are set forth in Table 3.

TABLE 3

| Specimen | Boyle's Law Method | X-Ray Fluorescence Method | Difference |
|---|---|---|---|
| 1 | 11.8 | 10.4 | −1.4 |
| 2 | 24.1 | 28.3 | +4.2 |
| 3 | 15.4 | 13.8 | −1.6 |
| 4 | 13.5 | 13.4 | −0.1 |
| 5 | 10.4 | 10.4 | 0 |
| 6 | 21.3 | 21.6 | +0.3 |
| Standard | 100.0 | 100.0 | — |

As shown in Table 3, results obtained by the X-ray fluorescence method in accordance with the invention usually agrees within ±2% with results obtained by the Boyle's Law Method. This agreement is comparable to what can be obtained by successive measures using the Boyle's Law Method.

Thus, the technique in accordance with the invention can permit the acquisition of data comparable to that obtained using Boyle's Law Method on much smaller samples. As is known, where core plugs are available, porosity can be measured using the Boyle's Law Method. However, core plugs are not always available. Cores are often not taken and well (drilling) cuttings may be the only samples available. Further, some cores cannot be tested for porosity plugs because they are required for engineering tests which require an intact core. In these cases and others, the technique in accordance with the invention permits obtaining measures of porosity from much smaller samples which are comparable to those obtained from core plugs using the Boyle's Law Method.

Further, the technique in accordance with the invention provides information of importance to the interpretation of electric logs by the explorationists. Thus, the measurement of total effective porosity is a fundamental measure of reservoir quality. Generally, reservoirs require total effective porosities of 6% or greater to meet economic criteria for production. Rocks having total effective porosities less than this will generally not be economic reservoirs for production. Of particular interest to exploration is the recognition of microporosity and its effects on the interpretation of electrical resistivity logs. Resistivity increases as the percentage of hydrocarbon-filled core space increases. Rocks having low resistivities, that is, those that are water-wet are generally noneconomic for petroleum production. However, rocks having a bimodal porosity distribution, that is, those having both macropores and micropores, may have low resistivity due to water bound in the micropores and nevertheless still produce hydrocarbons from the macroporous network so that the reservoir as a whole is economic to be produced. The X-ray fluorescence technique in accordance with the invention measures total effective porosity. Macroporosity can then be determined by methods known to those skilled in the art, for example, by point counting or image analysis. Total effective porosity minus macroporosity equals microporosity. Therefore, in accordance with the invention, it is possible to generate a measure of microporosity, which is important to the interpretation of electrical resistivity logs by the explorationists. This can, of course, be effected using samples of minimal size, as discussed in the previous paragraph.

Many changes can be made in specific means or steps for accomplishing the various features of the invention without departing from the concept of the invention disclosed herein. The invention is therefore not limited to the specific embodiments described herein as appropriate to meet requirements of law, but is defined in scope by the claims appended hereto and entitled to the range of equivalents permitted by law.

What is claimed is:

1. A method for determining total porosity of a rock sample comprising:
   stimulating an impregnated rock sample with X-ray electromagnetic radiation and detecting and measuring resulting X-ray fluorescence,
   the rock sample having been impregnated with a fluid under conditions effective for introducing the fluid into both macropores and micropores, and
   the fluid containing elements effective for fluorescing when stimulated by X-ray electromagnetic radiation;
   stimulating a sample comprising only the fluid containing elements effective for fluorescing and detecting and measuring the resulting fluorescence; and
   producing a measure of total effective porosity from the fluorescence resulting from the stimulated impregnated rock sample and fluorescence resulting from the sample comprising only the fluid.

2. The Method of claim 1 wherein:
   the fluid comprises an epoxy; and
   the elements contained in the fluid effective for fluorescing when stimulated by X-ray radiation are selected from the group consisting of chlorine, bromine, and iodine.

3. The Method of claim 2 wherein the power of X-ray radiation is effective for stimulating only the near surface of the sample in the range of less than 1000 angstroms in depth.

4. The Method of claim 1 wherein a beam of resulting fluorescence is detected at an take-off angle of about 90° relative to a sample.

5. The Method of claim 1 further comprising:
   generating a measure of macroporosity and deriving a measure of microporosity as the difference between total effective porosity measured in accordance with claim 1 and the measure of macroporosity.

6. The Method of claim 1 wherein the rock sample impregnated with the fluid and the sample comprising only the fluid are covered by a mask causing only a predetermined area of the samples to be subjected to X-ray radiation.

* * * * *